(12) United States Patent
Shapira

(10) Patent No.: US 6,798,461 B2
(45) Date of Patent: Sep. 28, 2004

(54) VIDEO SYSTEM FOR INTEGRATING OBSERVER FEEDBACK WITH DISPLAYED IMAGES

(76) Inventor: Shmuel Shapira, P.O. Box 1256, Sherwood, OR (US) 97140

( * ) Notice: Subject to any disclaimer, the term of this patent is extended or adjusted under 35 U.S.C. 154(b) by 154 days.

(21) Appl. No.: 10/143,343

(22) Filed: May 10, 2002

(65) Prior Publication Data

US 2003/0131351 A1 Jul. 10, 2003

Related U.S. Application Data

(60) Provisional application No. 60/346,637, filed on Jan. 10, 2002, and provisional application No. 60/352,223, filed on Jan. 29, 2002.

(51) Int. Cl.[7] .................................................. H04N 9/74
(52) U.S. Cl. ........................ 348/584; 348/584; 345/629
(58) Field of Search .................................. 348/584, 578, 348/571, 734, 552, 553, 460, 586, 598, 600, 585; 345/629, 632, 634, 636; H04N 9/74

(56) References Cited

U.S. PATENT DOCUMENTS 5,846,086 A  * 12/1998  Bizzi et al. .................. 434/247
5,896,164 A  *  4/1999  Orbach et al. ................. 725/12

* cited by examiner

Primary Examiner—Michael H. Lee
(74) Attorney, Agent, or Firm—Kolisch Hartwell, P.C.

(57) ABSTRACT

An interactive video system is provided that includes an input device configured to produce an input signal, and a video-mixing device configured to interpret the input signal and to receive a video-source signal. The video-mixing device includes a video-image processor configured to selectively alter the video-source signal based on the interpreted input signal and transmit a selectively altered-video signal.

4 Claims, 3 Drawing Sheets

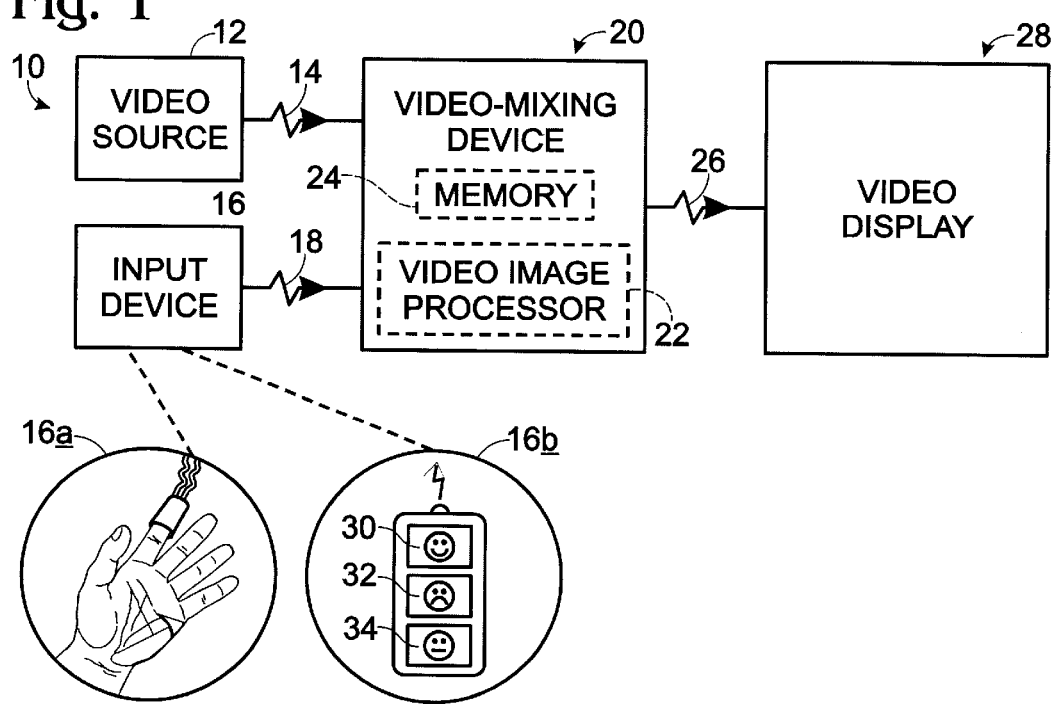
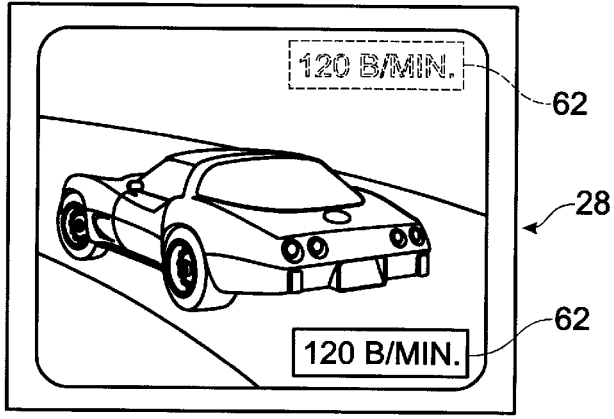
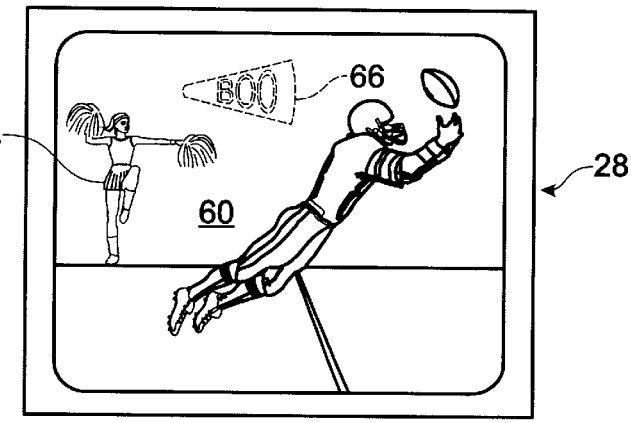

VIDEO SYSTEM FOR INTEGRATING OBSERVER FEEDBACK WITH DISPLAYED IMAGES

CROSS-REFERENCE TO RELATED APPLICATIONS

This application claims priority from U.S. Provisional Patent Application Ser. No. 60/346,637 entitled SYSTEM FOR PERSONALIZED TV, filed on Jan. 10, 2002, and U.S. Provisional Patent Application Ser. No. 60/352,223 entitled SYSTEM AND A METHOD FOR INTERACTIVE TV WATCHING, filed Jan. 29, 2002.

TECHNICAL FIELD

The present invention relates to a system for integrating observer feedback with displayed images. More particularly, the present invention relates to selectively altering a video image for displaying to an observer an image or images relating to the observer's emotional or physiological state.

BACKGROUND OF THE INVENTION

Biofeedback devices have been in use for some time now as a way of monitoring various physiological responses of the body. As used herein, biofeedback means a method for assisting a user to change or regulate a physiological or emotional process that the user is monitoring. Sophisticated instruments are often used to measure physiological responses and make them apparent to the patient, who then tries to alter and ultimately control them without the aid of monitoring devices. Biofeedback programs have been used to teach patients to relax muscles or adjust blood flow in the case of headache, to help partially paralyzed stroke victims activate muscles, and to alleviate anxiety in dental patients.

Biofeedback systems help people control physiological responses, which are usually involuntary, enabling people to control some of their physiological processes. The physiological responses the biofeedback systems detect are indicative of physiological and emotional processes. For example, skin resistance is used as an indicator of stress level. Changing skin resistance indicates a change in stress level. A user may learn to control stress by monitoring skin resistance on a biofeedback system. Biofeedback systems may be used for the treatment of a variety of health related conditions such as, but not limited to: asthma, incontinence, cardiac arrhythmias, hyperactivity, migraine headaches, and tension headaches. Biofeedback systems may be used to optimize fitness training, or as part of treatment and therapy regimes to manage stress.

Biofeedback systems may measure a variety of physiological responses, such as monitoring heart rate, respiration rate, conductance of the skin, pulse oxygen level, peripheral temperature, etc. Typically, biofeedback data is displayed on a dedicated display. Users of the biofeedback device may be able to easily monitor the display, but not be able to do other things at the same time, such as watch television.

The goal of a biofeedback therapy is to assist the user in recognizing certain actions that the user may take to regulate an undesired physiological or emotional process. Ultimately the user will be able to use the acquired skills during daily activities without an external feedback. Combining a biofeedback-based treatment with habitual television watching provides a transitional phase between practicing in isolation to a full exposure to situations associated with daily activities. Since TV watching generates a wide range of emotions in a controlled environment, it provides an opportunity for learning to cope with different emotional responses while a visual feedback is still available. In addition it may enhance a patient's overall enjoyment of the therapy process.

Additionally, with most television systems a viewer may only passively watch video content unable to incorporate any feedback into the video content. Expressing emotions and opinions in reaction to a TV program is entertaining and may as well have an emotional benefit as it assists in releasing emotions and draws awareness to emotions and reactions.

A system that enables a viewer to monitor biofeedback data on a television or similar display system, thereby permitting the viewer to watch video content and monitor the viewer's biofeedback response may be desirable.

SUMMARY OF THE INVENTION

An interactive video system is provided that includes an input device configured to produce an input signal, and a video-mixing device configured to interpret the input signal and to receive a video-source signal. The video-mixing device includes a video-image processor configured to selectively alter the video-source signal based on the interpreted input signal and transmit a selectively altered-video signal. The system may be used either as a tool in a feedback therapy session, or as a tool for facilitating active involvement of an observer in broadcasted programs.

BRIEF DESCRIPTION OF THE DRAWINGS

FIG. 1 is a schematic diagram of one embodiment of a video system according to the present invention.

FIG. 2 is a graphic representation of a video image selectively altered according to an embodiment of the present invention illustrating biofeedback data in a numerical format integrated in video content.

FIG. 5 is a graphic representation of an interactive video image according to another embodiment of the present invention illustrating user-selectable feedback data integrated in video content.

DETAILED DESCRIPTION OF THE PREFERRED EMBODIMENTS

Figure 3:
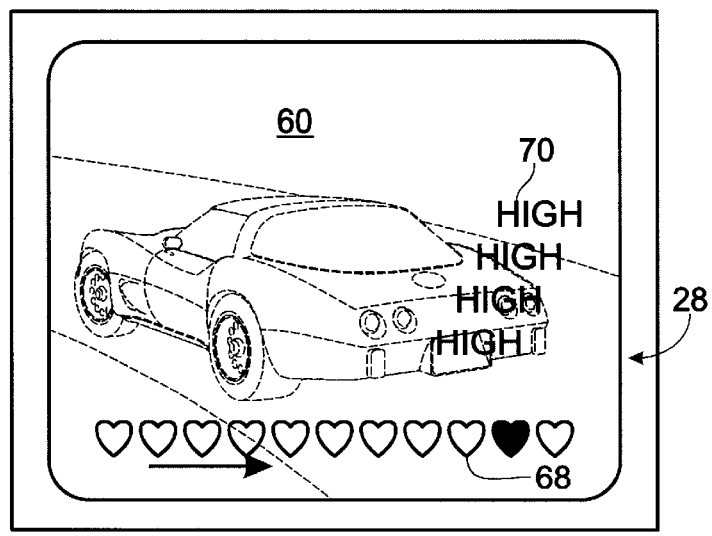
FIG. 3 is a graphic representation of a video image selectively altered according to another embodiment of the present invention illustrating biofeedback data in a graphical format integrated in video content.

One embodiment of the video system of the present invention is schematically depicted generally at 10 in FIG. 1. Video system 10 includes a video source 12 configured to generate a video-source signal 14. Video system 10 further includes an input device 16 configured to produce an input signal 18 and a video-mixing device 20 that may modify the video-source signal and transmit the modified signal to a display.

Video source 12 may be any suitable video source capable of producing a video signal, such as a television broadcast signal received via an antenna, a cable video signal transmitted from a cable provider, a video signal from a video cassette player or a digital video disc (DVD) player, or any similar analog, or digital video source. The video source 12 may be local, for example, a DVD player located proximate to video-mixing device 20, or the source may be remote, such as the cable broadcast delivered to a residence by a subscription cable company. Video source 12 produces a video-source signal 14. Video-source signal 14 may include image data, audio or sound data, and other formatting data or instructions. Video-source signal 14 may be digital or analog. When video-source signal 14 is analog it may use the video blanking interval to transmit formatting data or other instructions. It will be understood that any suitable video-source signal may be used with video-mixing device 20.

Input device 16 enables interaction between a viewer and the video system. The input device interfaces with video-mixing device 20. The interface may be via a direct-wired connection or it may be through a wireless transmission. Typically, the input device is configured to interact with a viewer either through a sensor or by user manipulation of a selector. Input device 16 may include any number of feedback sensors or selectors. Typically, input device 16 generates an input signal 18 that is transmitted to video-mixing device 20. Input signal 18 carries data to video-mixing device 20. The data may be dynamic, for example, it may include heart rate information that is updated at regular sampling intervals. The input signal may also transmit status information, formatting commands, and user-selectable data, as well as the aforementioned dynamic data.

Video-mixing device 20 may include programmable functions that may be selected through input device 16. For example, a user could use an on-screen menu system to set user-selectable parameters. The user-selectable parameters may be used to enhance the functionality of the video-mixing device. Programmable functions may include graphic options, such as, colors, shapes, sizes, images, positions on the display screen, and similar compositional elements. Furthermore, the user-selectable parameters may enable video system 10 to be customized for various tasks. For example, the parameters may determine what data received from a plurality of biofeedback sensors is displayed in the altered video content. Similarly, the user-selectable parameters may configure or enable the system to include input signals from a plurality of users.

Video-mixing device 20 receives video-source signal 14 from video source 12 and input signal 18 from input device 16. It will be understood that video-mixing device 20 may be configured to receive input from multiple input devices and from multiple viewers at the same time. Further, it will be understood that video-mixing device 20 may be configured to receive multiple video sources. The video-mixing device may then process both the input signal and the video-source signal in order to perform a variety of functions, some of which may be user programmable. Moreover, video-mixing device 20 may check the video-source signal for embedded instructions and data.

Video-mixing device 20 includes a video-image processor 22 that is configured to modify the video-source signal and enables the video-mixing device to produce an altered-video signal 26. The video-mixing device may include a microcontroller, a transceiver, a character generator, and an image generator to aid in image modification. The video-mixing device interprets input signal 18 and instructs video-image processor 22 to alter or modify the video signal. The video-mixing device may overlay images onto the video-source signal, or may integrate images into the video-source signal. An overlay image is positioned on top of the underlying video image. By contrast, an integrated image may alter the content of the video image instead of merely overlaying it. An integrated image may include a picture-in-picture and a change in picture size as well as other video image alteration.

As shown in FIG. 1, at 16a, input device 16 is a biofeedback sensor attached to the finger of a viewer. Biofeedback sensor 16a may sense the pulse rate of the viewer, or may detect other physiological information, including but not limited to heart rate, pulse oxygen level, blood pressure, respiration rate, peripheral skin temperature, skin conductance, temperature, electromicrograph data, electroencephalograms, etc. It will be understood that biofeedback sensor 16a may be attached to a different part of the viewer's body and may take a number of forms depending on the type of physiological data the sensor is designed to detect. Any physiological response may be monitored while watching video content. The input device sends the biofeedback data, for example the peripheral skin temperature, from the sensor to the video-mixing device as part of input signal 18. The video-mixing device interprets input signal 18 and integrates the temperature data into the video content image, thereby permitting the viewer to monitor their peripheral skin temperature while enjoying video content. It will be understood that input device 16a may be configured to gather an array of physiological responses and transmit the data gathered via input signal 18.

As discussed above, video-source signal 14 may include video image data and audio or sound data, as well as special instructions and data for the video-mixing device. The special instructions and data may enhance the functions of video-mixing device 20. By including special instructions for the video-mixing device embedded in video signal 14 the video-mixing device may locate any images generated in response to input signal 18 at a particular location on the video display. For example, a DVD may include instructions embedded in the video signal sent to the video-mixing device that locate an image based on the content of the images in the video-source signal. For example, as illustrated in FIG. 2, a data image 62 may be located by the embedded instructions in the video signal in the lower right hand corner of the screen initially, and then be moved by the embedded instructions to the upper right hand corner (data image 62 in dashed lines) as the video content changes. In this manner, the video-mixing device uses embedded instructions in the video-source signal to optimize the location of data image 62 to minimize the disruption of the video-source signal content displayed.

As illustrated in FIG. 3, a graphic 68 representing physiological response data from an input device of the type shown in FIG. 1, at 16a is shown. Graphic 68 is a series of hearts that may represent blood pressure, or some similar physiological response. A user may define thresholds for acceptable upper and lower limits for a specific type of physiological response. Once the limits have been set, the user may monitor their physiological responses while watching video content. If the response moves outside the threshold range an alert 70 will be triggered. The alert may be an audible noise or a visual symbol. As shown in FIG. 3, alert 70 is the word "HIGH" flashing across the content of the video. By setting these parameters, an at-risk patient may monitor their critical physiological responses easily while engaging in a leisure activity, such as watching television.

Figure 4:
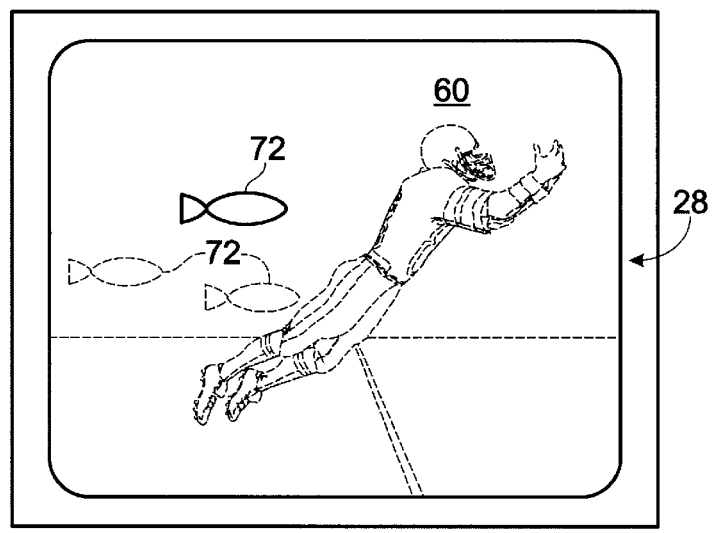
FIG. 4 is a graphic representation of an interactive video image according to another embodiment of the present invention illustrating biofeedback data in another graphical format integrated in video content.

As shown in FIG. 4, a moving graphic 72 is shown representing input data from an input device of the type shown in FIG. 1, at 16a. Using this configuration a viewer may receive biofeedback information as graphic 72 moves on the screen over video content 60. Graphic 72 moves as the physiological data received by the video-mixing device changes. For example, if a physiological response is increasing graphic 72 may move upward. Similarly, if a physiological response is decreasing graphic 72 may move downward. This movement may help a viewer control the monitored physiological response. Graphic 72 is shown for illustrative purposes as a fish.

Also as shown in FIG. 1, at 16b, input device 16 may be a wireless remote device. It will be understood that in another embodiment input device 16b may be hard wired to video system 10. Wireless remote device 16b enables the viewer to input responses to the video system. Device 16b may include selectors configured to register a level of intensity such as slider switches or dials. Behavioral responses such as pressure exerted on the selectors of the input device, length of time that a selector is engaged may be analyzed and displayed. Similarly, behavioral responses such as spatial position, direction of movement, range of movement, and speed of movement of the input device, as well as others behavioral responses may be analyzed and displayed. Additionally, device 16b may be configured to receive voice input corresponding to various emotional responses. User selection of a selector on device 16b causes the device to transmit the selection via input signal 18 to video-mixing device 20. The video-mixing device interprets input signal 18 and tells video-image processor 22 to alter video signal 14, as will be described in detail below.

It will be understood that device 16b may be configured to permit any desired type of user-selectable feedback. As a non-limiting example, shown in FIG. 1, remote device 16b may have a "pleased" selector 30 indicated by a smiling face, an "unpleased" selector 32 indicated by a frowning face, and an "apathetic" selector 34 indicated by an expressionless face. User selection of "pleased" selector 30 causes input device 16b to send a "pleased" signal to the video-mixing device. The video-mixing device interprets the input signal and instructs the video-image processor to alter the video-source signal to indicate the user is pleased. For example, by integrating an image associated with being pleased, such as a smiling face, into the altered-video signal.

Figure 6:
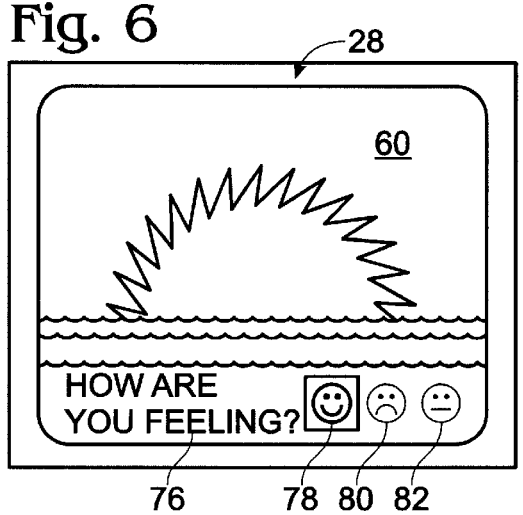
FIG. 6 is a graphic representation of an interactive video image according to another embodiment of the present invention illustrating user-selectable feedback data integrated in specialized video content.

As shown in FIG. 6, with reference to input device 16b, by selecting "pleased" button 30 during a football broadcast, a viewer causes the input device to send an input signal 18 containing a "pleased" indication to the video-mixing device. The video-mixing device interprets the "pleased" indication in the input signal and instructs the video-image processor to alter the video signal in order to display a celebrating cheerleader 64 integrated into the football game broadcast displayed at 60. It will be understood that user-selectable parameters may select the cheerleader image and associate it with a pleased indication on the input device. Moreover, the football broadcast signal may include image-formatting data that instructs the video-mixing device to integrate a cheerleader 64 into the altered video signal when a pleased input signal is detected. Similarly as shown in FIG. 6, a bullhorn 66 may be integrated into the football game broadcast when an "unpleased" indication is detected in the input signal.

Figure 7:
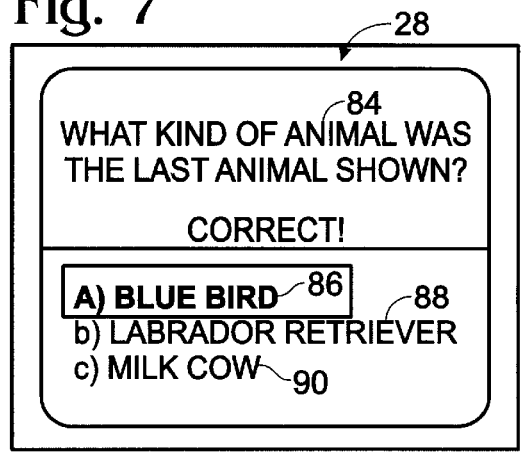
FIG. 7 is a graphic representation of an interactive video image according to another embodiment of the present invention illustrating user-selectable feedback data integrated in specialized video content.
Figure 8:
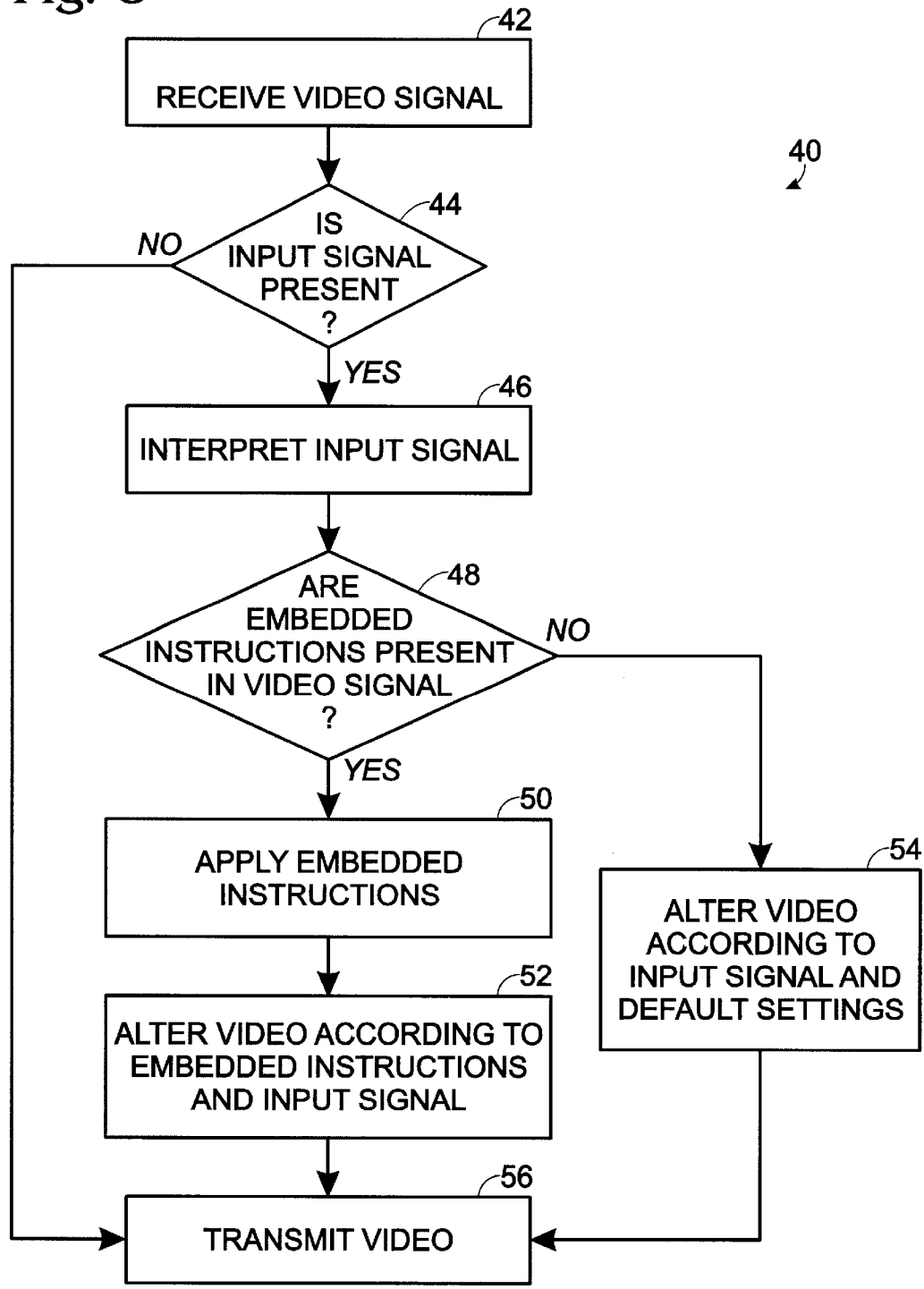
FIG. 8 is a flow chart showing a process that an embodiment of a video-mixing device according to the present invention uses for altering a video signal.

A capability enabled by embedding instructions and data in video-source signal 14, is an interactive question and answer capability, as illustrated by FIGS. 6 and 7. FIG. 6 illustrates a clinical evaluation tool enabled by video-mixing device 20, and FIG. 8 illustrates a quiz type interactive session that is enabled by video-mixing device 20.

It will be understood that a range of possible uses for embedded instructions and data in the video-source signal may be used including therapy specific instructions for specialized video content useful in treating certain affective disorders. For example, as shown in FIG. 6, video content 60 may be specialized to include prompts 76 for a viewer's response to the video content. The viewer may select from an input device, such as 16b, the answer that corresponds to their feelings about the content. As a non-limiting example, the content of FIG. 6, is shown as a sunrise. As shown, the user has selected a happy response 78 on display screen 28. Frowning button 32 on input device 16b corresponds to an unhappy response 80 on display screen 28. Apathetic button 34 on input device 16b corresponds to neutral response 82 on display screen 28. This type of system may be used in a clinical setting and a therapist may observe a patient interacting with the device to diagnose a patient.

Another example of embedded instructions in the video-source signal is shown in FIG. 7. A series of questions may be presented to a viewer. The viewer using an input device having a variety of selectors, such as the input device shown at 16b of FIG. 1, may respond to the questions presented. When the questions are communicated the viewer may respond using the input device. The viewer's response may be compared by video-mixing device 20 to embedded data in video-source signal 14. In response to the comparison the video-mixing device may command the video-image processor to modify the video signal. As shown in FIG. 7, a question 84 and a series of possible answers 86, 88, and 90 are displayed. A viewer inputs a selection using an input device similar to that shown at 16b, of FIG. 1. If the user selects the correct answer then, when the video-mixing device compares the user-selected answer from the input signal to the correct answer contained in the embedded instructions of the video-source signal, the video-mixing device instructs the video-image processor to alter the image to include the word "CORRECT" on the contents of display screen 28.

As another non-limiting example, if question 84 asked a user to identify a statement as true or false and the viewer correctly identified the statement as true, then an image indicating the response was correct may be included in altered-video signal 24 by video-mixing device 20. If, however, the viewer incorrectly identified the statement as false then an image indicating the response was incorrect may be included in the altered-video signal by video-mixing device 20.

Video system 10 may also provide assessment of compatibility between two or more people. For example, two or more people may watch the same video content and register their emotional response to the content. The system may record two peoples' physiological and emotional responses and compare the responses for compatibility. It will be understood that system could be used to determine a person's compatibility with a certain type of job or a specific situation.

Providing video-mixing device 20 with memory 24 and a communications port (not shown) enables many of these interactive functions to store a user's responses. The user or a clinician may download the response data after it has been gathered for more accurate assessment of a users condition. Moreover, video system 10 may include memory, and/or a mass storage device, and a communication link for storing and communicating data gathered by video-mixing device 20 during therapy sessions. This may enable a clinician to download data from a users system from a remote location over the communications link. This may be useful as a diagnostic tool for identifying emotion stressors. Therapists may review the stored data and identify issues of concern.

A method of analyzing video signals and input signals employed by video-mixing device 20 is shown generally in FIG. 8, at 40. Video-mixing device 20 typically receives a video signal from a video source at 42. The video-mixing device checks to determine if an input signal is detected at 44. If no input signal is detected the video signal received from the video source is transmitted to a display at 56. However, if an input signal is detected the video-mixing device interprets the input signal at 46. The video-mixing device checks the video signal received from the video source to determine if there are embedded instructions or data present in the video signal at 48. If no embedded instructions are present the video-mixing device instructs the video-image processor to alter the video-source signal according to the input signal and default settings at 54. After altering the video-source signal the video-mixing device transmits the video at 56. However, if there are embedded instructions in the video-source signal, the video-mixing device applies the embedded instructions at 50. The video-mixing device then instructs the video-image processor to alter the video-source signal according to the embedded instructions and input signal at 52. Finally, the video-mixing device transmits the altered-video signal to a display at 56.

The disclosure set forth above encompasses multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious and directed to one of the inventions. These claims may refer to "an" element or "a first" element or the equivalent thereof; such claims should be understood to include incorporation of one or more such elements, neither requiring nor excluding two or more such elements. Inventions embodied in other combinations and subcombinations of features, functions, elements, and/or properties may be claimed through amendment of the present claims or through presentation of new claims in this or a related application. Such claims, whether directed to a different invention or to the same invention, and whether broader, narrower, equal, or different in scope to the original claims, also are regarded as included within the subject matter of the inventions of the present disclosure.

I claim:

1. An interactive video system comprising:

an input device configured to produce an input signal;

a video-mixing device configured to interpret the input signal and to receive a video-source signal, wherein the video-mixing device includes a video-image processor configured to selectively alter the video-source signal based on the interpreted input signal and transmit a selectively altered-video signal;

wherein the video-mixing device is configured to read embedded instructions from the video-source signal, and wherein the video-source signal includes embedded instructions;

wherein the embedded instructions enable the video-mixing device to compare input signal responses to content of the video-source signal; and wherein the video-mixing device tracks comparisons between the input signal and the embedded instructions.

2. An interactive video system comprising:

an input device configured to produce an input signal;

a video-mixing device configured to interpret the input signal and to receive a video-source signal, wherein the video-mixing device includes a video-image processor configured to selectively alter the video-source signal based on the interpreted input signal and transmit a selectively altered-video signal;

wherein the video-mixing device is configured to read embedded instructions from the video-source signal, and wherein the video-source signal includes embedded instructions;

wherein the embedded instructions enable the video-mixing device to compare input signal responses to content of the video-source signal; and wherein the video-mixing device tracks comparisons between input signals from a plurality of users.

3. A method of integrating observer feedback with video images comprising:

receiving a video-source signal;

receiving an input signal from a user;

selectively modifying the video-source signal based on the input signal;

transmitting to a display device, the selectively modified video-source signal;

wherein the video-source signal includes embedded instructions;

wherein embedded instructions enable a video-mixing device to compare input signal responses to content of the video-source signal;

wherein the video signal includes a series of questions for a viewer to respond to and the embedded instructions enable the video-mixing device to score viewer responses to the series of questions; and wherein the video-mixing device tracks comparisons between the input signal and the embedded instructions.

4. A method of integrating observer feedback with video images comprising:

receiving a video-source signal;

receiving an input signal from a user;

selectively modifying the video-source signal based on the input signal;

transmitting to a display device, the selectively modified video-source signal;

wherein the video-source signal includes embedded instructions;

wherein embedded instructions enable a video-mixing device to compare input signal responses to content of the video-source signal;

wherein the video signal includes a series of questions for a viewer to respond to and the embedded instructions enable the video-mixing device to score viewer responses to the series of questions; and wherein the video-mixing device tracks comparisons between input signals from a plurality of users.

* * * * *